US011168076B2

(12) United States Patent
Eady et al.

(10) Patent No.: US 11,168,076 B2
(45) Date of Patent: Nov. 9, 2021

(54) SURFACTANTS FROM ALDEHYDES

(71) Applicant: Sironix Renewables, Inc., Seattle, WA (US)

(72) Inventors: Shawn Eady, Seattle, WA (US); Christoph Krumm, Seattle, WA (US)

(73) Assignee: SIRONIX RENEWABLES, INC., Seattle, WA (US)

( * ) Notice: Subject to any disclaimer, the term of this patent is extended or adjusted under 35 U.S.C. 154(b) by 0 days.

(21) Appl. No.: 17/124,635

(22) Filed: Dec. 17, 2020

(65) Prior Publication Data

US 2021/0188824 A1 Jun. 24, 2021

Related U.S. Application Data

(60) Provisional application No. 62/952,708, filed on Dec. 23, 2019.

(51) Int. Cl.
*C07D 407/06* (2006.01)
*C11D 1/26* (2006.01)

(52) U.S. Cl.
CPC .............. *C07D 407/06* (2013.01); *C11D 1/26* (2013.01)

(58) Field of Classification Search
CPC .................................................. C07D 407/06
See application file for complete search history.

(56) References Cited

U.S. PATENT DOCUMENTS

| | | | |
|---|---|---|---|
| 2,411,567 | A | 11/1946 | Fisher |
| 4,443,559 | A | 4/1984 | Smith, Jr. |
| 4,477,382 | A | 10/1984 | Goel et al. |
| 5,338,517 | A | 8/1994 | Evans, III et al. |
| 5,387,705 | A | 2/1995 | Stipp et al. |
| 5,776,320 | A | 7/1998 | Marion et al. |
| 6,149,879 | A | 11/2000 | Forestiere et al. |
| 6,416,659 | B1 | 7/2002 | Groten et al. |
| 2004/0260137 | A1 | 12/2004 | Elomari et al. |
| 2015/0150768 | A1 | 6/2015 | West et al. |
| 2015/0166596 | A1 | 6/2015 | Hill |
| 2017/0226075 | A1 | 8/2017 | Stensrud et al. |
| 2018/0051113 | A1 | 2/2018 | Yang et al. |

FOREIGN PATENT DOCUMENTS

| | | |
|---|---|---|
| CN | 104162447 B | 11/2017 |
| WO | 9627580 A1 | 9/1996 |
| WO | 2017079718 A1 | 5/2017 |
| WO | 2017079719 A1 | 5/2017 |
| WO | 2019040389 A1 | 2/2019 |

OTHER PUBLICATIONS

Dorwald et al., Side reactions in Organic Synthesis, Wiley: VCH Weinheim Preface, pp. 1-15 and Chapter 8, pp. 279-308. (Year: 2005).*
Liang et al., "Acid-Catalyzed Ring Opening of Furan in Aqueous Solution," Energy Fuels, vol. 32, No. 4, 2018, pp. 4139-4148.
Joseph, "Tunable Synthesis and Characterization of Oleo-Furan Sulfonate Surfactants from Renewable Furan and Fatty Acids," Dissertation submitted to the Faculty of University of Minnesota, May 2018, pp. 1-154.
Park et al., "Tunable Oleo-Furan Surfactants by Acylation of Renewable Furans," ACS Central Science, vol. 2, Issue 11, Oct. 19, 2016, pp. 820-824.
Pubchem. CID 68119, Retrieved from the Internet <https://pubchem.ncbi.nlm.nih.gov/compound/68119>, Mar. 26, 2005, pp. 1-19.
Ackman et al., "Ozonolysis of Unsaturated Fatty Acids I. Ozonolysis of Oleic Acid," Canadian Journal of Chemistry, vol. 39, No. 10, 1961, pp. 1956-1963.
Kadesch, "Ozonolysis of Fatty Acids and Their Derivatives," Progress in the Chemistry of Fats and other Lipids vol. 6, 1963, pp. 291-312.
Lundin et al., "Intensified and Safe Ozonolysis of Fatty Acid Methyl Esters in Liquid CO2 in a Continuous Reactor," AIChE Journal, vol. 63, No. 7, 2017, pp. 2819-2826.
Saedi et al., "MIL-101 metal-organic framework: A highly efficient heterogeneous catalyst for oxidative cleavage of alkenes with H2O2," Catalysis Communications, vol. 17, Jan. 5, 2012, pp. 18-22.
Travis et al., "Osmium Tetroxide-Promoted Catalytic Oxidative Cleavage of Olefins: An Organometallic Ozonolysis," Journal of the American Chemical Society, vol. 124, No. 9, 2002, pp. 3824-3825.
Bidange et al., "Ethenolysis: A Green Catalytic Tool to Cleave Carbon-Carbon Double Bonds," Chemistry A European Journal, vol. 22, No. 35, Aug. 22, 2016, pp. 12226 12244.
Byrne et al., "Tools and techniques for solvent selection: green solvent selection guides," Sustainable Chemical Processes, vol. 4, No. 7, 2016, 24 pages.
Pubchem. CID 54467179, Retrieved from the Internet <https://pubchem.ncbi.nlm.nih.gov/compound/54467179>, Dec. 4, 2011, pp. 1-6.
Shi et al., "Au—Pd nanoparticles on layered double hydroxide: Highly active catalyst for aerobic oxidation of alcohols in aqueous phase," Catalysis Communications, vol. 18, Feb. 2012, pp. 142-146.
Almqvist, "Furans from biomass: Production, applications and techno economic potential," Processum, Apr. 20, 2018, 9 pages.
Froidevaux et al, "Study of the Diels-Alder and retro-Diels-Alder reaction between furan derivatives and maleimide for the creation of new materials," RSC Advances, vol. 5, 2015, pp. 37742-37754, Abstract Only.

(Continued)

Primary Examiner — Patricia L Morris
(74) Attorney, Agent, or Firm — Fredrikson & Byron, P.A.

(57) ABSTRACT

Methods for synthesizing oleo-furan surfactants from fatty aldehydes and compositions of furan based surfactants synthesized from such methods are disclosed. One method of forming a surfactant can include a hydroxyalkylation reaction of two methylfuran molecules with a fatty aldehyde molecule to form a di-furan product. This method can also include forming a surfactant from the di-furan product formed from the hydroxyalkylation. In particular, this di-furan product can be a surfactant precursor that is functionalized to form a surfactant.

10 Claims, 2 Drawing Sheets

(56) References Cited

OTHER PUBLICATIONS

Gandini, "The furan/maleimide Diels-Alder reaction: A versatile click-unclick tool in macromolecular synthesis," Progress in Polymer Science, vol. 38, No. 1, Jan. 2013, pp. 1-29, Abstract Only.

Gheneim et al., "Diels-Alder reactions with novel polymeric dienes and dienophiles: synthesis of reversibly cross-linked elastomers," Macromolecules, vol. 35, No. 19, Aug. 8, 2002, pp. 7246-7253, Abstract Only.

Saha et al., "Advances in 5-hydroxymethylfurfural production from biomass in biphasic solvents," Green Chemistry, vol. 16, 2014, pp. 24-38.

Trubyanov et al., "High-pressure distillation: Simultaneous impact of pressure, temperature and loading on separation performance during distillation of high-purity gases in high-performance randomly-packed columns," Separation and Purification Technology, vol. 135, Oct. 2014, pp. 117-126.

Yow et al., "Hydrolysis of palm olein catalyzed by solid heteropolyacids," Journal of the American Oil Chemists' Society, vol. 79, 2002, pp. 357-361.

Ben-Daniel et al., "Selective Aerobic Oxidation of Alcohols with a Combination of a Polyoxometalate and Nitroxyl Radical as Catalysts," Journal of Organic Chemistry, vol. 66, No. 25, Nov. 2001, pp. 8650-8653.

Brown et al., "The Condensation of Furan and Sylvan with Some Carbonyl Compounds," Canadian Journal of Chemistry, vol. 34, No. 9, Sep. 1956, pp. 1147-1153.

Corberan et al., "Green oxidation of fatty alcohols: Challenges and opportunities," Applied Catalysis A: General, vol. 474, Mar. 2014, pp. 211-223.

Hong et al., "Selective oxidation of octadecan-1-ol to octadecanoic acid over Co3O4/SiO2 catalysts," Reaction Kinetics and Catalysis Letters, vol. 81, Jan. 2004, pp. 13-20.

Iovel et al., "Hydroxymethylation of Furan and its Derivatives in the Presence of Cation-Exchange Resins," Journal of Molecular Catalysis, vol. 57, No. 1, 1989, pp. 91-103.

Kan et al., "Catalytic oxidation of α-eicosanol into eicosanic acid in the presence of Ti-MCM-41 or active component supported Ti-MCM-41 catalysts," Microporous and Mesoporous Materials, vol. 44-45, Apr. 2001, pp. 609-617.

Sakuth et al., "Reactive Distillation," Ullmann's Encyclopedia of Industrial Chemistry, Jan. 1, 2012, Wiley-VCH, Weinheim, pp. 263-276.

Engel et al., "Thermoreversible reactions on inorganic nanoparticle surfaces: Diels-Alder reactions on sterically crowded surfaces," Chemistry of Materials, vol. 25, Dec. 12, 2012, pp. 149-157.

Naik et al., "Liquid phase acylation of 2-methylfuran with fatty acid anhydride," NAM 26, 2019 North American Catalysis Society Meeting, Jun. 26, 2019, 3 pages.

Pubchem, Compound Summary for SID 150925859, Modify Date: Jun. 3, 2019 [retrieved on Apr. 13, 2021]. Retrieved from the Internet: <URL: https://pubchem.ncbi.nlm.nih.gov/substance/150925859>, 7 pages.

Vauthier et al., "Interfacial Diels-Alder reaction between furan-functionalized polymer coatings and maleimide-terminated poly-(ethylene glycol)," The Journal of Physical Chemistry C, vol. 123, Jan. 22, 2019, pp. 4125-4132.

International Patent Application No. PCT/US2020/065489, International Search Report and Written Opinion dated Mar. 18, 2021, 6 pages.

Liu et al., "Molybdenum Oxide-Modified Iridium Catalysts for Selective Production of Renewable Oils for Jet and Diesel Fuels and Lubricants," ACS Catalysis, vol. 9, Jul. 16, 2019, pp. 7679-7689.

Park et al., "Tunable Oleo-Furan Surfactants by Acylation of Renewable Furans," ACS Central Science, vol. 2, Oct. 19, 2016, pp. 820-824.

Pubmed Compound Record for CID 14421037, '2-Ethyl-5-hexylfuran-3-sulfonic acid', U.S. National Library of Medicine, Feb. 9, 2007, (https://pubchem.ncbi.nlm.nih.gov/compound/14421037), pp. 1-10.

\* cited by examiner

SURFACTANTS FROM ALDEHYDES

RELATED APPLICATION

This application claims the benefit of, and priority to, U.S. Provisional Patent Application No. 62/952,708 filed Dec. 23, 2019.

TECHNICAL FIELD

This disclosure generally relates to compositions of furan based surfactants as well as methods for forming furan based surfactants. In particular, furan based surfactant compositions, and methods for synthesizing such furan based surfactants, disclosed herein include di-furan surfactants from fatty aldehydes.

BACKGROUND

Surfactants are chemical compounds that have a variety of applications. Such applications can include household cleaners and detergents, institutional & industrial cleaning products, agricultural chemicals such as spray adjuvants, oilfield applications, and various coating additives. Short for surface active agent, a surfactant consists of a hydrophilic moiety, which attracts water, and a hydrophobic moiety, which attracts oil and dirt. The amphiphilic structure of surfactant molecules enables them to suspend dirt, emulsify, and modify surface properties of materials. Variations in the chemical structure of a surfactant molecule can enable tunable properties, such as emulsifying capability (hydrophilic/lipophilic balance), oil/dirt suspension capacity (critical micelle concentration), cold water performance (Krafft point), foaming, and biodegradation.

Surfactants have generally been synthesized from petrochemical feedstocks, such as long chain alkanes/alkenes and ethylene oxide. However, surfactants synthesized from petrochemical feedstocks can present a number of issues. For one, such surfactants include chemicals that can be harmful to the environment. Moreover, such surfactants may not perform as intended in certain applications. For example, despite decades of development, these various surfactant structures are faced by a unified problem—the presence of hard water (e.g., containing calcium, magnesium, iron, etc.) inactivates these surfactants. When inactivation occurs, this causes surfactants to form solid precipitates and substantially lose the intended functionality.

To address these issues associated with surfactants synthesized from petrochemical feedstocks, surfactants are beginning to be derived from natural sources, such as coconut oil and palm kernel. The development has mainly focused on replacing the petrochemical surfactants with bio-based analogues having identical chemical structure (e.g., sodium lauryl sulfate from petroleum and sodium coco sulfate from coconut oil). The result is a surfactant that is more eco-friendly relative to petrochemical surfactants. Moreover, to solve the problem of surfactant inactivation in the presence of hard water, a new class of bio-based surfactants, called oleo-furan surfactants ("OFS" or "OFSs") has been developed. In fact, OFSs have demonstrated 50-100 times greater calcium tolerance compared with other surfactants.

While OFSs solve issues associated with surfactants synthesized from petrochemical feedstocks, the sources and synthesis processes currently used to derive OFSs may hamper the value of OFSs because they may make it difficult for OFSs to compete economically with the cost of petrochemical surfactants.

SUMMARY

The present disclosure describes the hydroxyalkylation of furan with a fatty aldehyde to form a di-furan product. This di-furan product can then be functionalized to form a variety of surfactants as suitable for particular applications. Notably, up to this point, the hydroxyalkylation of furan with a fatty aldehyde has not been considered as a feasible means by which to synthesize oleo-furan surfactants. More specifically, the hydroxyalkylation of furan with a relatively long chain (e.g., $C_4$ or greater) fatty aldehyde to produce a di-furan precursor (that can be tuned to create a useful oleo-furan surfactant) has not been recognized because there has not been a suitable mechanism to couple such fatty aldehyde and furan components. The present disclosure describes exemplary embodiments of suitable mechanisms to couple such fatty aldehyde and furan components and thereby ultimately provides the ability to produce useful resulting oleo-furan surfactant structures.

In general, various exemplary embodiments disclosed herein include a method for synthesizing oleo-furan surfactants containing a di-furan moiety from variable chain length fatty aldehydes and one of a number of furan derivatives. In addition, various exemplary embodiments disclosed herein include resulting surfactant chemical structures synthesized by the described reactions. As noted, the present disclosure provides embodiments of an oleo-furan surfactant synthesis process that utilizes a unique chemical mechanism to couple the fatty aldehyde and furan components and thereby yield a unique di-furan surfactant precursor that can be functionalized to form various surfactants useful in different applications. Such embodiments disclosed herein may thereby ultimately allow oleo-furan surfactants to be more economically competitive with traditional petrochemical surfactants while still providing environmentally friendly and hard-water tolerance benefits of oleo-furan surfactants over petrochemical surfactants.

One exemplary embodiment includes a method (e.g., a method of forming a surfactant). This method embodiment can include performing a hydroxyalkylation reaction. This hydroxyalkylation reaction can include the hydroxyalkylation of two methylfuran molecules with a fatty aldehyde molecule to form a di-furan product. For example, the di-furan product formed from the hydroxyalkylation can be of the formula (1) shown below. The fatty aldehyde used in the hydroxyalkylation reaction can be of a variety of variable chain lengths, including various long chain aldehydes, such as $C_2$ or greater, $C_3$ or greater, $C_4$ or greater, $C_5$ or greater, $C_6$ or greater, $C_7$ or greater, $C_8$ or greater, $C_9$ or greater, or $C_{10}$ or greater. One example of a fatty aldehyde that can be used in the hydroxyalkylation reaction to form the di-furan product is a saturated fatty aldehyde, such as lauric aldehyde derived from coconut or palm oil-sourced lauric alcohols or carboxylic acids. In addition to the hydroxyalkylation, the method can include forming a surfactant from the di-furan product formed from the hydroxyalkylation. In particular, this di-furan product can be a surfactant precursor that is functionalized to form a surfactant tuned for a variety of applications.

Another exemplary embodiment includes a method. For example, the method can be a method of forming a surfactant. This exemplary method can include the step of performing a hydroxyalkylation of two furan molecules with a fatty aldehyde molecule to form a di-furan product. And, this method can include the step of forming a surfactant from the di-furan product.

In a further embodiment of this method, the fatty aldehyde molecule used in the hydroxyalkylation is a long chain aldehyde. For example, in this further method embodiment, the long chain aldehyde can have a chain length of $C_2$ to $C_{28}$. As another example, the long chain aldehyde can have a chain length of $C_4$ to $C_{28}$. In either of these two examples, in this further method embodiment the two furan molecules can be two furan aromatic moieties. Also in this further method embodiment, the fatty aldehyde can be a saturated fatty aldehyde. For example, the saturated fatty aldehyde can be a lauric aldehyde derived from one of oil-sourced lauric alcohols or carboxylic acids. For instance the oil-sourced lauric alcohols can include at least one of coconut oil and palm oil.

In a further embodiment of this method, the two furan molecules can be methylfuran molecules. And, in this further method embodiment, the saturated fatty aldehyde can be a lauric aldehyde.

In a further embodiment of this method, the di-furan product formed from the hydroxyalkylation is a compound having the formula (1)

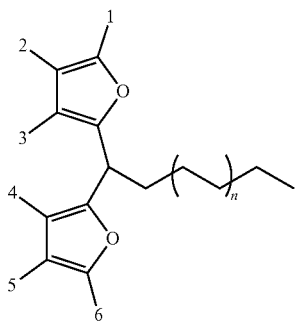

(1)

wherein n is an extended saturated alkyl chain from 0 to 28 carbon atoms in length, and wherein at least one of labels 1-6 is a functional group selected from the group consisting of: —H, —CH$_3$, —CH$_2$CH$_3$, an alkyl chain, —OH, sulfonate, sulfate, amine, functional group listed in Table 1, and functional group listed in Table 2.

For example, in this further method embodiment, n is an extended saturated alkyl chain from 4 to 28 carbon atoms in length. For example, the surfactant can be formed from the compound having the formula (1) by adding at least one hydrophilic functional group to any one or more of the positions labeled 1-6.

As another example, in this further method embodiment, the compound is:

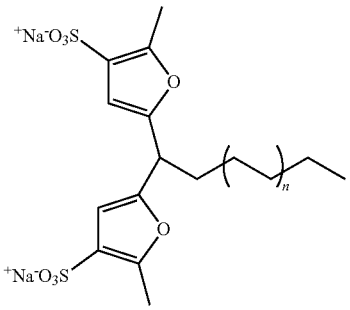

As an additional example, in this further method embodiment, the compound is:

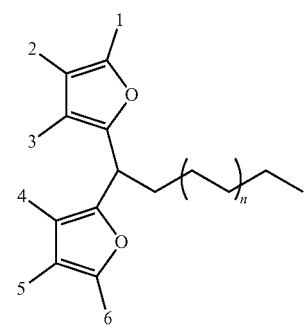

Another embodiment includes a compound having the formula (1)

(1)

where n is an extended saturated alkyl chain from 0 to 28 carbon atoms in length, for instance such as n being an extended saturated alkyl chain from 4 to 28 carbon atoms in length, and where at least one of labels 1-6 is a functional group selected from the group consisting of: —H, —CH$_3$, —CH$_2$CH$_3$, an alkyl chain (e.g., a longer alkyl chain), —OH, sulfonate, sulfate, amine, functional group listed in Table 1, and functional group listed in Table 2. For instance, as one exemplary embodiment, where n is an extended saturated alkyl chain from 4 to 28 carbon atoms in length, at least one of labels 1-6 can be sulfonate.

In a further such embodiment, the compound having the formula (1) is as follows:

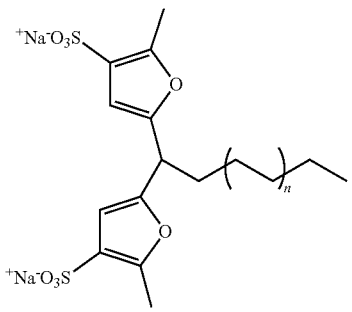

In another further such embodiment, the compound having the formula (1) is as follows:

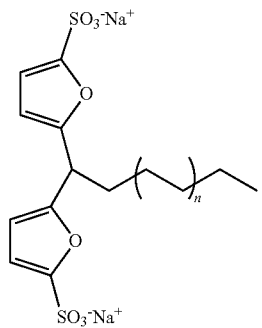

BRIEF DESCRIPTION OF DRAWINGS

The following drawings are illustrative of particular embodiments of the present invention and, therefore, do not limit the scope of the invention. The drawings are intended for use in conjunction with the explanations in the following description. Embodiments of the invention will be described in conjunction with the appended drawings, wherein like reference characters denote like elements.

DETAILED DESCRIPTION

Figure 1:
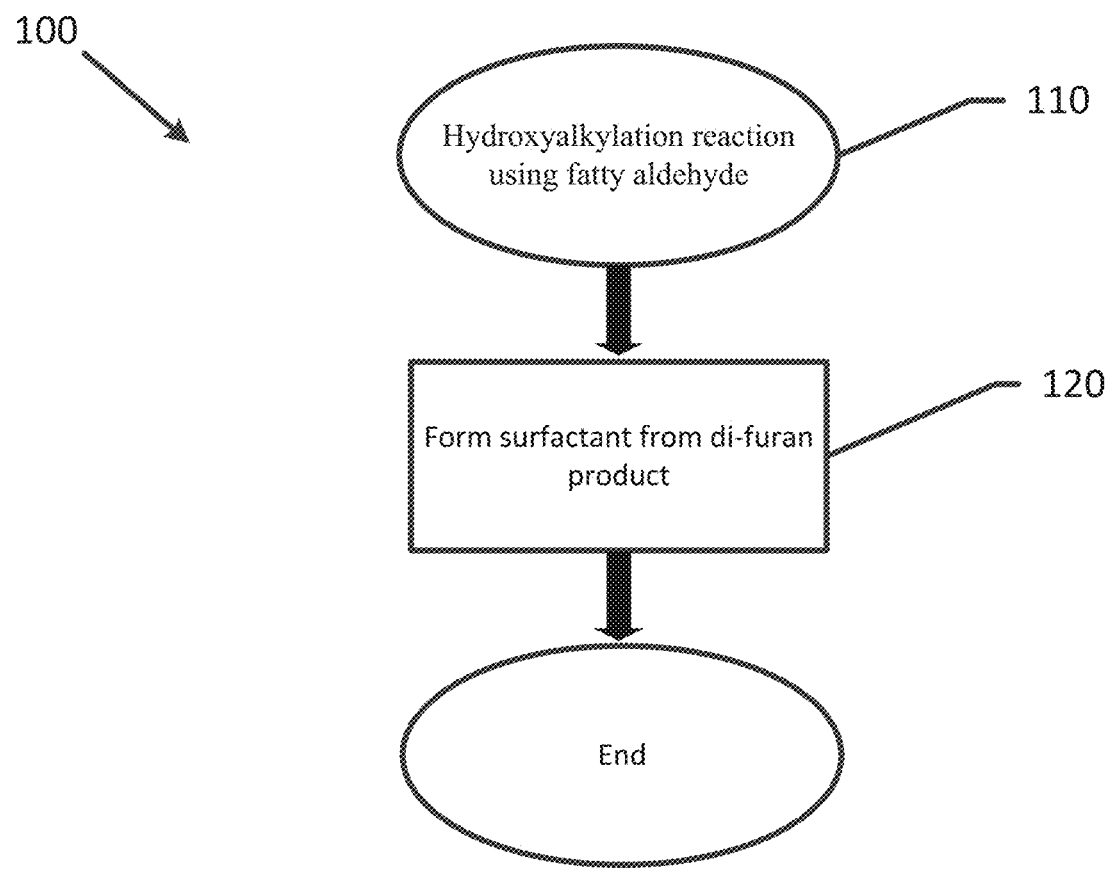
FIG. 1 is a flow diagram of an embodiment of a method of forming a di-furan product using a fatty aldehyde.

The following detailed description is exemplary in nature and is not intended to limit the scope, applicability, or configuration of the invention in any way. Rather, the following description provides some practical illustrations for implementing exemplary embodiments of the present invention. Examples of elements, materials, compositions, and/or steps are provided below. Though those skilled in the art will recognize that many of the noted examples have a variety of suitable alternatives that are also within the scope of the present disclosure.

As described herein, embodiments of the present disclosure can utilize a fatty aldehyde to from a di-furan product. This di-furan product can then be functionalized to form a variety of surfactants as suitable for particular applications. In particular, the present disclosure describes exemplary embodiments that include the hydroxyalkylation of furan with a fatty aldehyde (e.g., a relatively long chain (e.g., $C_4$ or greater, $C_5$ or greater, $C_6$ or greater, $C_7$ or greater, $C_8$ or greater, $C_9$ or greater, or $C_{10}$ or greater) fatty aldehyde) to produce a di-furan precursor that can be functionalized to produce various ole-furan surfactants.

One exemplary embodiment of a synthesis process is depicted below as Scheme 1. Scheme 1 illustrates an exemplary reaction for synthesis of a di-furan dianionic surfactant from a fatty aldehyde. In Scheme 1, "n" is used to designate an extended saturated alkyl chain 0-28 carbons in length. For example, in some embodiments of Scheme 1, "n" can be an extended saturated alkyl chain 4-28 carbons in length.

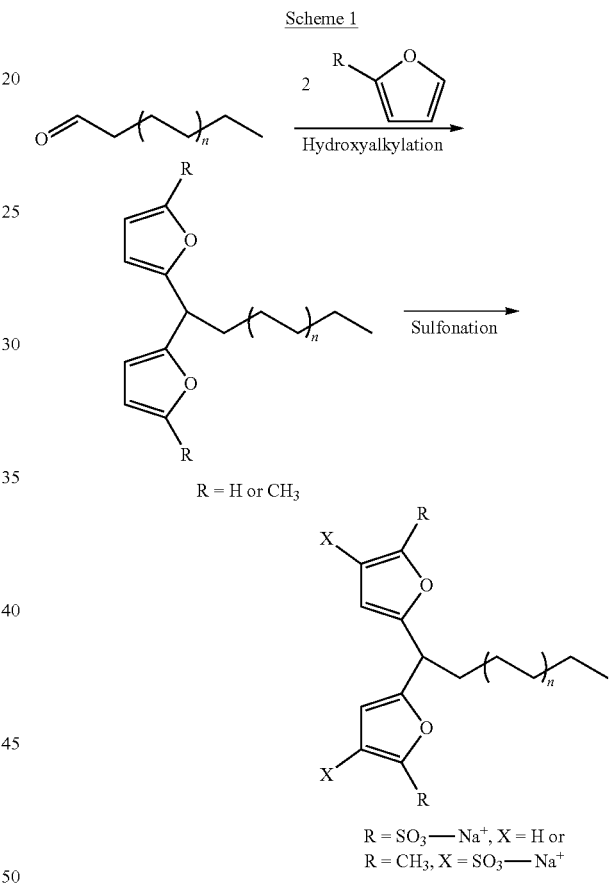

The exemplary embodiment shown in Scheme 1 includes hydroxyalkylation of two methylfuran molecules with a faux aldehyde molecule to form a di-furan product.

Scheme 1 shows a specific embodiment of a di-furan product formed by hydroxyalkylation of two methylfuran molecules with a fatty aldehyde molecule.

However, the di-furan product formed in Scheme 1 by the hydroxyalkylation of two methylfuran molecules with a fatty aldehyde molecule can more generally be of General Structure 1, shown below. In General Structure 1, each numbered position (1-6) designates a functional group, such as —H, —$CH_3$, —$CH_2CH_3$, a longer alkyl chain, —OH, or other functional group and "n" designates an extended saturated alkyl chain 0-28 carbons in length, such as embodiments where "n" designates an extended saturated alkyl chain 4-28 carbons in length.

General Structure 1

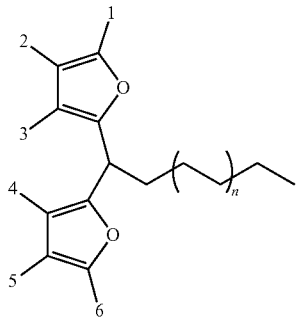

Any of the various embodiments of General Structure 1 can then be functionalized into a surfactant, for instance by adding hydrophilic functional groups to any one or more numbered positions 1-6 (including various combinations of added hydrophilic functional groups to any one or more numbered positions 1-6). Examples of added functional groups that can be included in General Structure 1 are any one or more of sulfates, sulfonates, alcohols, ethoxylates, propoxylates, amines, or other functional groups listed in Tables 1 and 2 below.

Table 1 lists examples of ionic moieties that can make up the hydrophilic portion of the surfactant in General Structure 1. Table 2 lists examples of non-ionic moieties that can make up the hydrophilic portion of the surfactant in General Structure 1.

TABLE 1

| Anionic | | Cationic | |
|---|---|---|---|
| Ionic Moieties | | | |
| Sulfate | R—O—S(=O)(=O)—O⁻ | Amines & Ammonium salts | R*—N⁺(R)(R*)—R* |
| Sulfonate | R—S(=O)(=O)—O⁻ | | (cyclic N⁺ with R, R*) |
| Sulfinate | R—S(=O)—O⁻ | | (cyclic N⁺ with X, R, R*) |
| Thiosulfate | R—O—S(=O)(=S)—O⁻ | Polyammonium | [R—N⁺(R*)(R*)—R*—N⁺(R*)(R*)—R*] |
| Sulfamidate | R—N(H)—S(=O)(=O)—O⁻ | Hydroxyammonium | R—N⁺(OH)(R*)—R* |
| Carboxylate | R—C(O⁻)=O⁻ | Pyridinium | (pyridinium-N⁺—R) |
| Sarcosinate | R*(R)N—R'—C(=O)—O⁻ | Picolinium | R*—(picolinium-N⁺—R) |
| Taurate | R*(R)N—*R—S(=O)(=O)—O⁻ | Imidazaolinium | (imidazolinium with R, R*, R*) |
| Phosphate | R—O—P(=O)(O⁻)—O⁻ or R—O—C(=O)—O—R*, O⁻ | Benzimidazolinium | (benzimidazolinium with R*, R*, R*) |

TABLE 1-continued

| | Anionic | | Cationic | |
|---|---|---|---|---|
| Pyrophosphate | R–O–P(=O)(O⁻)–O–P(=O)(O⁻)–O–R* | | Oxonium | R–O⁺(R*)(R*) |
| Phosphonate | R–P(=O)(O⁻)–R* <br> or <br> R–P(=O)(O⁻)–O⁻ | | Sulfonium | R–S⁺(R*)(R⁻) |
| | | | Phosphonium | R–P⁺(R*)(R*)(R*) |

| Counter-ion | |
|---|---|
| Na⁺, K⁺, Li⁺, Ca²⁺, Mg²⁺, NH₄⁺, amines | Cl⁻, Br⁻, NO₃⁻, SO₄²⁻, PO₄³⁻, HPO₄²⁻, H₂PO₄⁻, CH₃OSO₃⁻, HCO₂⁻, CH₃CO₂ |

- Pyrophosphate: $R\text{–}O\text{–}P(=O)(O^-)\text{–}O\text{–}P(=O)(O^-)\text{–}O\text{–}R^*$
- Phosphonate: $R\text{–}P(=O)(O^-)\text{–}R^*$ or $R\text{–}P(=O)(O^-)\text{–}O^-$
- Oxonium: $R\text{–}\overset{+}{O}(R^*)\text{–}R^*$
- Sulfonium: $R\text{–}\overset{+}{S}(R^*)\text{–}R^-$
- Phosphonium: $R\text{–}\overset{+}{P}(R^*)(R^*)\text{–}R^*$
- Counter-ions: $Na^+, K^+, Li^+, Ca^{2+}, Mg^{2+}, NH_4^+$, amines; $Cl^-, Br^-, NO_3^-, SO_4^{2-}, PO_4^{3-}, HPO_4^{2-}, H_2PO_4^-, CH_3OSO_3^-, HCO_2^-, CH_3CO_2$

TABLE 2

| Non-ionic moieties | |
|---|---|
| Polyethoxylate | $R\text{–}(OCH_2CH_2)_n\text{–}OR$ |
| Poly(Oxyethylene-co-Oxypropyiene) | |
| 1 | $R\text{–}(OCH_2CH_2)_m\text{–}(OCHCH_2)_n\text{–}(OCH_2CH_2)_m\text{–}OH$ with CH₃ branch on middle block |
| 2 | $R\text{–}(OCHCH_2)_n\text{–}(OCH_2CH_2)_m\text{–}(OCHCH_2)_n\text{–}OH$ with CH₃ branches on outer blocks |
| 1,4-Sorbitan derivatives | (tetrahydrofuran ring with OR, OR, OR, and CH(OR)CH₂OR substituents) |
| Isosorbide derivatives | (bicyclic isosorbide with two OR groups) |
| Polyglycoside | (repeating glucoside unit with OH, OH, CH₂OH substituents, terminated by OR) |

TABLE 2-continued

| Non-ionic moieties |
|---|
| Hydroxyl, methoxy, carboxyl, or alkanal groups 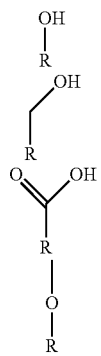 |

Referring back to Scheme 1, in some embodiments Scheme 1 can use a saturated fatty aldehyde, such as lauric aldehyde, derived from, for instance, coconut or palm oil-sourced lauric alcohols or carboxylic acids, to synthesize surfactants.

Scheme 2 illustrates a further exemplary reaction for synthesis of a surfactant using a saturated fatty aldehyde. In Scheme 2, the numbered position (4) designates the alkyl chain length in this embodiment.

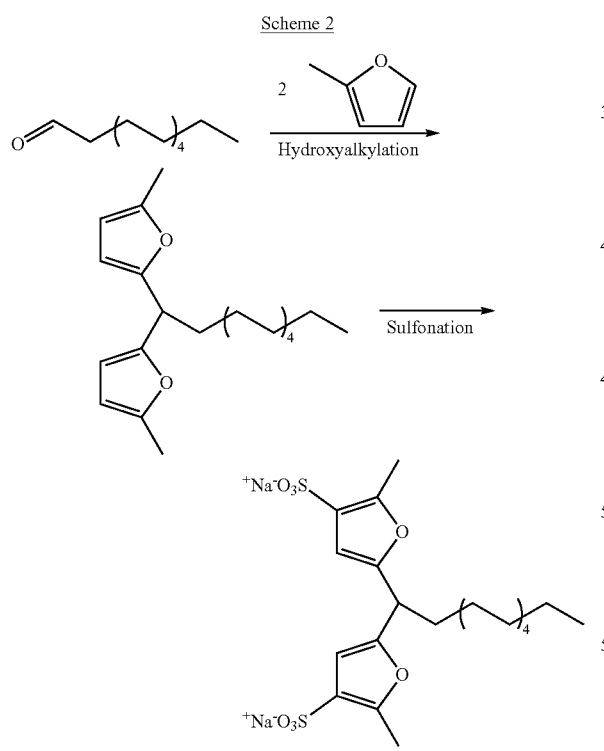

Scheme 2

The exemplary embodiment shown in Scheme 2 uses lauric aldehyde as the saturated fatty aldehyde to synthesize a surfactant from the lauric aldehyde and 2-methylfuran. In the embodiment shown in Scheme 2, the sulfonation produces a specific embodiment of a surfactant chemical structure, shown in above in Scheme 2, of that shown previously as General Structure 1.

Alternately, a distribution of fatty acids with varying alkyl chain length and varying degrees of unsaturation can be used, for instance such as those obtained from soybean oil. Formation of the fatty aldehydes can be achieved, for example, through the oxidation of fatty alcohols, the reduction of fatty acids, or any additional chemical modification of biomass-derived feedstocks. Hydroxyalkylation of the furan moieties by the fatty aldehyde can produce a di-furan compound, which is subsequently functionalized with a hydrophilic group such as a sulfonate.

The fatty aldehydes used for synthesis of a di-furan compound may be prepared by a number of methods. Scheme 3 shows two examples of methods for preparing the fatty aldehydes used to synthesize a di-furan compound includes oxidation of fatty alcohols and the reduction of fatty acids. In Scheme 3, "n" designates an extended saturated or unsaturated, alkyl chain 0-28 carbons in length. For example, in some embodiments of Scheme 3. "n" can designate an extended saturated or unsaturated, alkyl chain 4-28 carbons in length.

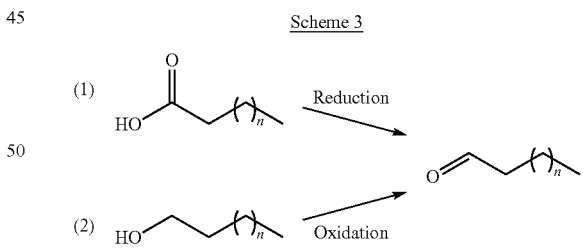

Scheme 3

The exemplary preparation shown in Scheme 3 prepares fatty aldehydes by reduction of fatty acids at (1) or oxidation of fatty alcohols at (2).

Alternatively, two fatty aldehydes can be yielded from a single molecule of monounsaturated fatty acid by cleaving the double bond. Scheme 4 shows one example of such a method of yielding two fatty acids that includes olefin metathesis and ozonolysis. In Scheme 4, "m" and "n" designate extended saturated alkyl chains of variable length (e.g., 4-28 carbons in length.).

Scheme 4

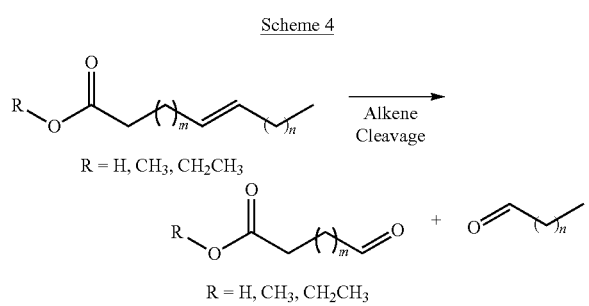

The exemplary preparation shown in Scheme 4 prepares fatty aldehydes by alkene cleavage of monosaturated fatty acids.

In an analogous manner to the alkene cleavage of a monounsaturated fatty acid, such methods can also be employed to yield three or more aldehydes from a polyunsaturated fatty acid.

The following description provides exemplary details relating to hydroxyalkylation and sulfonation reactions steps included in the embodiments, such as Schemes 1 and 2, described previously.

As noted, various synthesis embodiments, such as each of Scheme 1 and Scheme 2, can include a hydroxyalkylation reaction. The hydroxyalkylation of two furan aromatic moieties with a fatty aldehyde results in formation of the di-furan hydrocarbon complex. During the hydroxyalkylation of two furan aromatic moieties with a fatty aldehyde, two carbon-carbon bond formations occur between each aromatic moiety and the α-carbon of the aldehyde. The hydroxyalkylation of two furan aromatic moieties with a fatty aldehyde can result in loss of one equivalent $H_2O$ when forming the di-furan hydrocarbon complex.

Such hydroxyalkylation of two furan aromatic moieties with a fatty aldehyde to form the di-furan product has not been considered using long chain (e.g., $C_4$ or greater, $C_5$ or greater, $C_6$ or greater, $C_7$ or greater, $C_8$ or greater, $C_9$ or greater, or $C_{10}$ or greater) aldehydes. Moreover, one of ordinary skill in the art would not have any reason to believe that hydroxyalkylation of two furan aromatic moieties with a long chain fatty aldehyde would reasonably lead to formation of the di-furan product given the unpredictable nature of modifying a hydroxyalkylation reaction to include long chain aldehydes.

The hydroxyalkylation reaction can be facilitated in a variety of manners. For instance, the hydroxyalkylation reaction can be facilitated by a wide variety of acid catalysts. Suitable exemplary acid catalysts can include inorganic acids, such as hydrochloric and sulfuric acid, organic acids, such as acetic acid, or solid acids such as resins or zeolites. The hydroxyalkylation reaction can be performed in a temperature range from 0-120° C. in a variety of organic solvents. For example, suitable organic solvents can include hydrocarbons, such as hexane or heptane. Though in some cases the hydroxyalkylation reaction can take place in the absence of solvent (neat). For instance, the use of solid acid catalysts in the absence of solvent can be useful for enabling higher conversion, less furanic degradation, and easier separation of catalyst from product, while the use of moderately low temperatures (0-60° C.) can be useful to avoid side product formation. Use of excess furan reagent to the aldehyde can be useful both to improve diffusion without diluting the reagent and to improve conversion, with molar ratios of 5-20 furan reagent to fatty aldehyde being usable. As one specific example, an acidic resin, including, for instance, Amberlyst-15, Amberlyst-36, Dowex 50Wx4, or Amberlite IRC-50, is stirred in neat furan reagent at 0° C. with slow addition of 1 mole fatty aldehyde for every 10 moles furan reagent. Then, the temperature is slowly increased to 50° C. and agitation is continued until no fatty aldehyde is detected in solution. The acid catalyst can then be filtered out of the reaction solution, and the residual furan reagent can be removed by rotary evaporation, with potential for reuse of both regenerated acid catalyst and distilled furan reagent.

As also noted, various synthesis embodiments can include a sulfonation reaction. The sulfonation of the reduced or non-reduced di-furan surfactant precursor can be performed at scale using, for example, previously developed $SO_3$-air reaction or via other sulfonation methods, such as $SO_3$-pyridine.

One or more of the described reaction steps in any of the above depicted Schemes can use one or more catalysts. When a catalyst is implemented, the described reactions can be carried out using any of the catalysts listed in Table 3 shown below. Table 3 shows exemplary catalyst classes along with associated types that can be used for any one or more (e.g., all) of the reactions in the Schemes disclosed herein.

TABLE 3

| Family | Catalyst Type | Examples |
| --- | --- | --- |
| Acids | Metal halides | $AlCl_3$, $TiCl_4$, $FeCl_3$, $BF_3$, $SnCl_4$, $ZnCl_2$, $ZnBr_2$ |
| | Mineral acids | HCl, HBr, HI, $HClO_4$, $HClO_3$, $HNO_3$, $H2SO_4$, $H_3PO_4$ |
| | Organic acids | $CH_3COOH$, $CF_3OOH$ |
| | Ion exchange resins | Amberlyst, Nafion |
| | Zeolites | H-ZSM5, H-BEA, H—Y, Mordernite, Ferrierite, MWW |
| | Metal-substituted zeolites | Sn, Ge, Ti, Fe, Zr, Mo, Cu, Ni (possible substituents) |
| | Mesoporous materials | MCM-41, MCM-48, SBA-15, SPP (also with metal-substitution, e.g., Sn) |
| | Metal oxides | $SiO_2$, $Al_2O_3$, $ZrO_2$, $TiO_2$, $SiO_2$—$Al_2O_3$ |
| | Sulfated metal oxides | $SO_3$—$ZrO_2$, $SO_3$—$TiO_2$, $SO_3$—$SnO_2$ |
| | Mixed metal oxides | $SiO_2$—$ZrO_2$, $SiO_2$—$Al_2O_3$, zeolites-$ZrO_2$, $Al_2O_3$—$ZrO_2$, $WOx$—$ZrO_2$ |
| | Carbon | Sulfated carbon |
| | Phosphates | $NbOPO_4$, $ZrO_2$—$PO_4$, Nb—P—Si—O |
| | Heteropolyacids | $H_3PW_{12}O_{40}$, $H_3SiW_{12}O_{40}$, $H_3PMo_{12}O_{40}$, $H_3SiMo_{12}O_{40}$ (also with metal-substitution, e.g., Cs) |

Also with respect to the reaction steps in the Schemes disclosed herein, various feedstock materials and solvents can be used. Feedstocks used in the process can include, for example, but are not limited to fatty aldehydes, fatty alcohols and fatty acids with chain lengths varying from, for instance $C_4$ to $C_{28}$, triglycerides both mixed and homotriglycerides with chains lengths varying from $C_4$ to $C_{28}$ that can be saturated or unsaturated (mono-, di-, or tri-), furan or furan derivatives such as methylfuran, ethylfuran, or furfural, and solvents.

Solvents used for separations can be ketones including acetone and methylethylketone, hydrocarbons including but not limited to pentane, hexane, and heptane, cyclohexane, and cyclopentane, aromatic organics including benzene, toluene, organic nitriles including acetonitrile, propionitrile, and butyronitrile, organic chlorocarbons including dichloromethane, dichloroethane, chloroform, alcohols including but not limited to methanol, ethanol, and isopropanol, ethereal solvents including but not limited to dimethyl ether, diethyl ether, and tetrahydrofuran, esters including but not limited to methyl acetate and ethyl acetate, water and finally the absence of solvent (neat).

In some embodiments of the Schemes disclosed herein, solvent use may be limited to or more solvent selection guides outlined by Byrne and coworkers, including but not limited to acetone, heptane, cyclohexane, toluene, xylene, acetonitrile, methanol, ethanol, isopropanol, 1-butanol, ethyl acetate and isopropyl acetate, cyclopentyl methyl ether, 2-methyltetrahydrofuran, tetrahydrofuran, water and finally the absence of solvent (neat).

In some embodiments, solvent use will be limited by one or more solvent selection guides. For example, in some embodiments, solvent use will be limited by one or more solvent selection guides outlined in Byrne, F. P., et al., Tools and Techniques for Solvent Selection: Green Solvent Selection Guides, *Sustainable Chemical Processes* 2016 4(7). Such solvents may include, though are not limited to, acetone, heptane, cyclohexane, toluene, xylene, acetonitrile, methanol, ethanol, isopropanol, 1-butanol, ethyl acetate and isopropyl acetate, cyclopentyl methyl ether, 2-methyltetrahydrofuran, tetrahydrofuran, and water. Though it is also noted that this could instead occur in the absence of solvent (i.e. neat). In one particular embodiment, solvent use will be limited to those accepted by all solvent selection guides outlined in Byrne, F. P., et al., Tools and Techniques for Solvent Selection: Green Solvent Selection Guides, *Sustainable Chemical Processes* 2016 4(7). Such solvents including 1-butanol, isopropyl acetate, and water. Though, again, it is noted that this could instead occur in the absence of solvent (i.e. neat).

FIG. 1 shows a flow diagram of an embodiment of a method 100 of forming a di-furan product using a fatty aldehyde. The method 100 can include one or more of the synthesis actions described previously.

At step 110, the method 100 includes a hydroxyalkylation reaction. The hydroxyalkylation reaction at step 110 can include the hydroxyalkylation of two methylfuran molecules with a fatty aldehyde molecule to form a di-furan product. For example, the di-furan product formed from the hydroxyalkylation at step 110 can be of General Structure 1 shown above.

As described elsewhere herein, various fatty aldehydes can be used in the hydroxyalkylation reaction at step 110 to form the di-furan product. The fatty aldehyde used in the hydroxyalkylation reaction at step 110 can be of a variety of variable chain lengths. In a number of embodiments, the fatty aldehyde used in the hydroxyalkylation reaction at step 110 can be a long chain aldehyde, such as $C_4$ or greater, $C_5$ or greater, $C_6$ or greater, $C_7$ or greater, $C_8$ or greater, $C_9$ or greater, or $C_{10}$ or greater. One example, described previously herein, of a fatty aldehyde that can be used in the hydroxyalkylation reaction at step 110 to form the di-furan product is a saturated fatty aldehyde, such as lauric aldehyde derived from coconut or palm oil-sourced lauric alcohols or carboxylic acids.

At step 120, the method 100 included forming a surfactant from the di-furan product formed at step 110. The di-furan product formed at step 110 can be a surfactant precursor that is functionalized at step 120 to form a surfactant. For example, when step 110 forms the di-furan product of General Structure 1, one or more hydrophilic functional groups can be added to any one or more of numbered positions (1-6). Suitable such functional groups can include sulfates, sulfonates, alcohols, ethoxylates, propoxylates, amines, or other functional groups listed in Tables 1 and 2.

As indicated previously, embodiments disclosed herein can include chemical compositions. Such chemical compositions include di-furan products formed from fatty aldehydes as well as surfactants formed by functionalizing such di-furan products.

One example chemical structure is depicted above as General Structure 1. General Structure 1 represents a new class of oleo-furan surfactants including a di-furan moiety from variable chain length fatty aldehydes. Namely, this new class of di-furan surfactants represented by General Structure 1 includes two furan moieties acting as part of a hydrophilic head on one end and the hydrophobic alkyl chain on the other.

In embodiments of General Structure 1, the alkyl chain length between furan molecules can vary, for example, from n=0 to n=12 ($C_4$ to $C_{28}$, respectively). The particular chain length can be determined, for instance, based on the intended application of the surfactant of General Structure 1. For example, in certain such embodiments of General Structure 1, the alkyl chain length between furan molecules can be in the alkyl chain range of n=0 to n=7 ($C_4$ to $C_{18}$, respectively), such as being in the alkyl chain range of n=1 to n=7 ($C_6$ to $C_{18}$, respectively) or in the alkyl chain range of n=2 to n=5 ($C_8$ to $C_{14}$, respectively). In other such embodiments of General Structure 1, the alkyl chain length between furan molecules can vary, for example, from $C_4$ to $C_{28}$, for instance from $C_4$ to $C_{28}$, $C_5$ to $C_{28}$, $C_6$ to $C_{28}$, $C_7$ to $C_{28}$, $C_8$ to $C_{28}$, $C_3$ to $C_{18}$, $C_4$ to $C_{18}$, $C_5$ to $C_{18}$, $C_6$ to $C_{18}$, $C_7$ to $C_{18}$, and $C_8$ to $C_{18}$ in length.

Notably, the length of the alkyl chain can drastically change surfactant characteristics. For example, the length of the alkyl chain can drastically change surfactant characteristics that impact performance in various applications (e.g., laundry detergency). Thus, alkyl chain length between furan molecules in embodiments of General Structure 1 can be considered as an important surfactant structural feature. Accordingly, alkyl chain lengths in one range (e.g., $C_1$-$C_3$) can be considered to produce surfactants with significantly different application performance than those in another range (e.g., $C_4$-$C_{28}$). Evidence of these alkyl chain length-dependent differences in surfactant function can be observed in Table 3 further below. For this reason, even minor changes in alkyl chain length can result in significant differences in surfactant characteristics.

Functional groups designated by numbered positions (1-6) in General Structure 1 can be —H, —$CH_3$, —$CH_2CH_3$, a longer alkyl chain, —OH, sulfonate, sulfate, amine, or other functional group listed in Table 1 or Table 2. In particular, in certain further embodiments, these functional groups would include —$CH_3$, sulfonate, sulfate, polyglycoside, and polyethoxylate. Even more particularly, in further such embodiments, these functional groups would include —$CH_3$ and sulfonate.

Depicted below are Structure 1A and Structure 1B. Structure 1A and Structure 1B are each one example of a structure that adheres to the more general formula of General Structure 1. Depending on the particular application for which a surfactant is intended to be used, Structure 1A and Structure 1B can be preferred structures embodying the general formula of General Structure 1. The use of "n" designates an extended saturated alkyl chain 0-24 carbons in length. For example, Structure 1A and Structure 1B can each have an alkyl chain length between furan molecules in the range of the number of carbons described above.

Structure 1A of General Structure 1

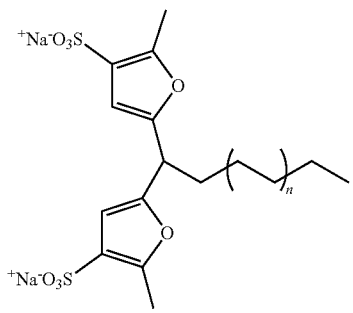

Structure 1B of General Structure 1

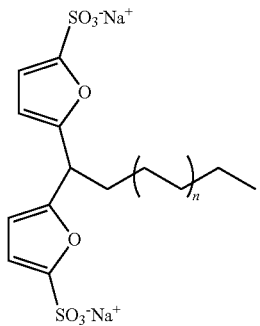

Each of Structure 1A and Structure 1B is an embodiment of General Structure 1 and thus is part of the new class of oleo-furan surfactants including a di-furan moiety from variable chain length fatty aldehydes.

EXAMPLES

The following provides an illustrative, non-limiting example of a method of synthesis and related synthesized structure.

A dianionic furan surfactant according to Structure 1A of General Structure 1 was formed and is depicted below as Example Surfactant 1.

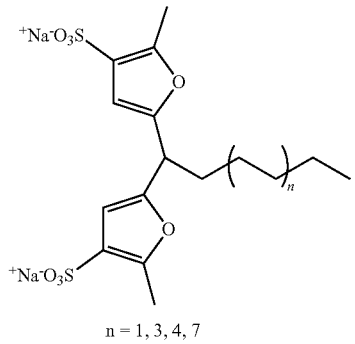

n = 1, 3, 4, 7

In forming Example Surfactant 1, the hydroxyalkylation of 2 equivalents 2-methylfuran (>99%, Alfa Aesar) with lauric aldehyde (99%, Sigma) was carried out in an ice bath in the presence of Amberlyst-15 catalyst (Alfa Aesar). Sulfonation of the surfactant precursor was carried out under ambient atmosphere with elevated temperature in acetonitrile solvent (99.5%, Alfa Aesar) using pyridine sulfur trioxide (Alfa Aesar) as the sulfonating agent.

Example Surfactant 1, shown above, has had certain performance characteristics assessed. For instance, various performance metrics of the synthesized Example Surfactant 1 were measured, including the time required for Example Surfactant 1 solution to wet cotton fabric, the amount of foam Example Surfactant 1 generates when agitated, the tolerance of Example Surfactant 1 to calcium ions in solution as a measure of surfactant performance in hard water, and the temperature below which Example Surfactant 1 forms a solid precipitate, known as the Krafft Point. These metrics are listed in Table 4 below.

TABLE 4

| Alkyl Chain Length (n) | Krafft Point (° C.) | Cotton Wetting Time (sec)[†] | Foam Height (mm)[‡] | Turbid Concentration (mM)* |
|---|---|---|---|---|
| 6 (1) | <0 | >300 | 140/125 | >500 |
| 10 (3) | <0 | >300 | 140/137 | >500 |
| 12 (4) | <0 | 41 | 131/125 | 100 |
| 18 (7) | <0 | >300 | 33/1 | 25 |

[†]Time required for a 0.1 wt % surfactant solution to wet a cotton skein (purchased from TestFabrics). Test performed according to ASTM D2281-10

[‡]Height of foam layer produced in a 0.25 wt % surfactant solution initially and after 5 minutes standing. Test conducted according to ASTM D1173-07

*Calcium tolerance of the surfactant, defined here as the lowest calcium chloride concentration at which precipitate persists in a 0.1 wt % surfactant solution The performance metrics set forth in Table 4 show differences in performance as a function of alkyl chain length. For example, the amount of foam Example Surfactant 1 generates and its calcium tolerance decreases at the longest alkyl chain length tested (i.e. $C_{18}$) while an intermediate alkyl chain length ($C_{12}$) was observed to have the highest rate of fabric wetting (a useful metric in laundry detergency applications).

Figure 2:
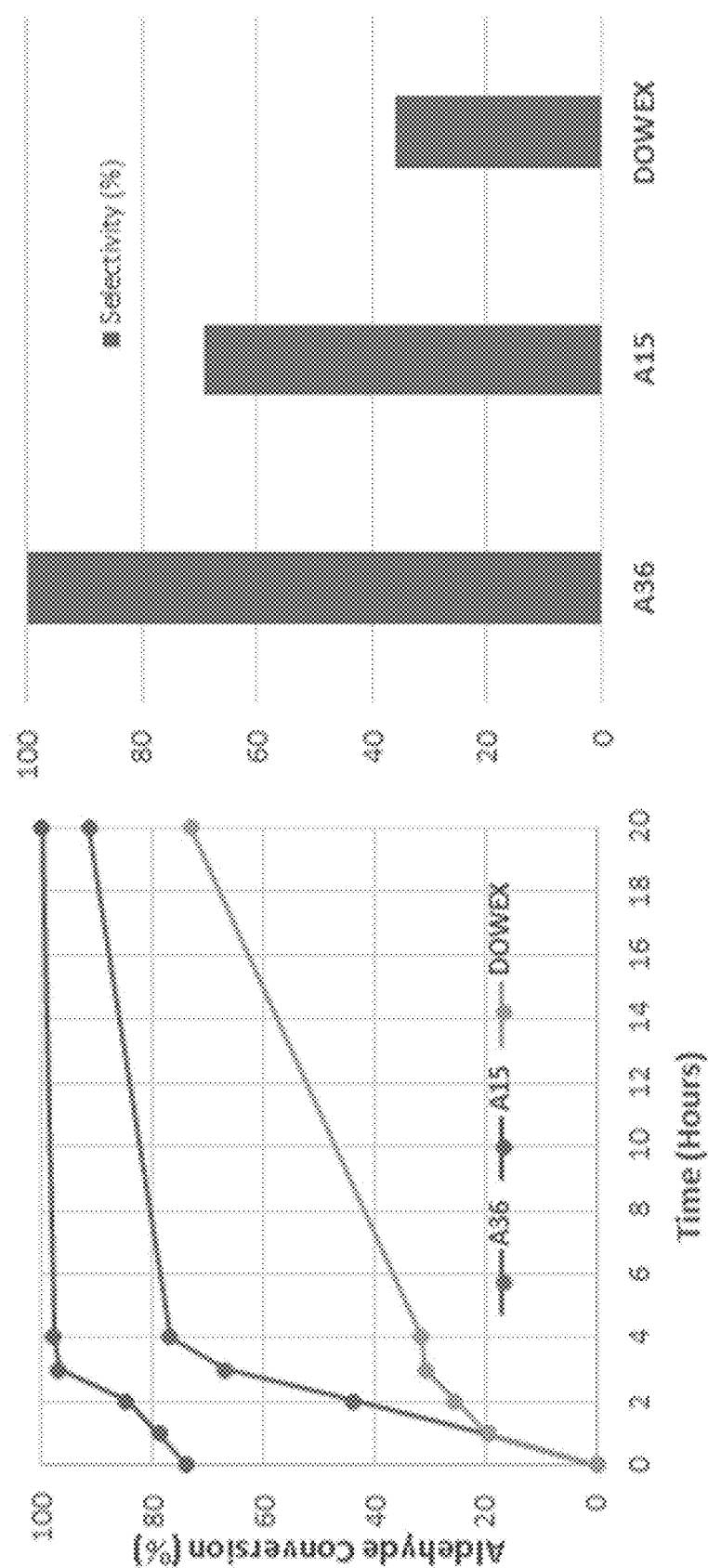
FIG. 2 is a conversion plot (left-hand side) and selectivity bar graph (right-hand side) resulting from the use of three different acid catalysts: Amberlyst-36 ("A36"), Amberlyst-15 ("A15"), and DOWEX 50WX2-400 ("DOWEX").

As another example, the impact of acid catalyst selection for the hydroxyalkylation reaction was also assessed, using 2-methylfuran and dodecanal (lauric aldehyde, C12 alkyl chain) as the furan and fatty aldehyde, respectively. In this series of reactions, an excess of 10 molar equivalents 2-methylfuran (>99%, Alfa Aesar) was combined with 1 equivalent lauric aldehyde (99%, Sigma) and 1 equivalent of the selected acid catalyst. The reaction was performed under ambient atmosphere with an initial temperature of 0° C., which was elevated to and maintained at 50° C. for the 20 hour duration of the reaction. FIG. 2 illustrates a conversion plot (left-hand side below) and selectivity bar graph (right-hand side below) resulting from the use of 3 different acid catalysts, Amberlyst-36 ("A36"), Amberlyst-15 ("A15"), and DOWEX 50WX2-400 ("DOWEX").

As can be seen in the conversion plot (left-hand side above), at time equal twenty hours, DOWEX has the lowest conversion percentage (approximately 75%), A15 has the highest conversion percentage (approximately 100%), and A36 has a conversion percentage (approximately 93%) between that of DOWEX and A15. Thus, the performance metrics set forth in FIG. 2, above, show differences in both hydroxyalkylation conversion and selectivity. For example. Amberlyst-15 (A15) was observed to consume nearly 100% of the aldehyde after only 4 hours, compared to the approximately 80% and approximately 30% conversion at 4 hours for Amberlyst-36 (A36) and DOWEX 50WX2-400 (DOWEX), respectively. However, selectivity to the di-furan reaction product was sub-optimal for A15 (approximately 70%) and DOWEX (approximately 35%) catalysts; only A36 provided approximately quantitative selectivity. These findings suggest catalyst tuning can have a material impact on reaction efficiency and yield.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A method comprising the steps of:
performing a hydroxyalkylation of two furan molecules with a fatty aldehyde molecule to form a di-furan product; and
forming a surfactant from the di-furan product,
wherein the di-furan product formed from the hydroxyalkylation is a compound having the formula (1):

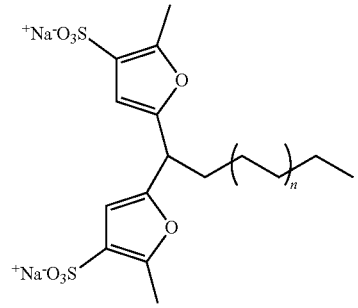

(1)

wherein n is an extended saturated alkyl chain from 0 to 28 carbon atoms in length.

2. A compound having the formula (1):

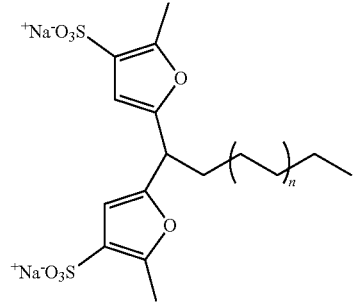

(1)

wherein n is an extended saturated alkyl chain from 0 to 28 carbon atoms in length.

3. The method of claim 1, where n is equal to 1.
4. The method of claim 1, wherein n is equal to 3.
5. The method of claim 1, wherein n is equal to 4.
6. The method of claim 1, wherein n is equal to 7.
7. The compound of claim 2, wherein n is equal to 1.
8. The compound of claim 2, wherein n is equal to 3.
9. The compound of claim 2, wherein n is equal to 4.
10. The compound of claim 2, wherein n is equal to 7.

* * * * *